United States Patent [19]
Tanzer et al.

[11] Patent Number: 5,342,333
[45] Date of Patent: Aug. 30, 1994

[54] ABSORBENT ARTICLE CONTAINING AN ANHYDROUS DEODORANT

[75] Inventors: Richard W. Tanzer; Mary A. Bruemmer; Anthonette A. Gossens, all of Neenah, Wis.

[73] Assignee: Kimberly-Clark Corporation, Neenah, Wis.

[21] Appl. No.: 20,027

[22] Filed: Feb. 18, 1993

Related U.S. Application Data

[63] Continuation of Ser. No. 685,363, Apr. 15, 1991, abandoned, which is a continuation-in-part of Ser. No. 428,085, Oct. 27, 1989, Pat. No. 5,037,412, which is a continuation-in-part of Ser. No. 354,337, May 23, 1989, abandoned, which is a continuation-in-part of Ser. No. 213,399, Jun. 30, 1988, abandoned.

[51] Int. Cl.$^5$ ............................................. A61F 13/15
[52] U.S. Cl. .................................. 604/359; 604/358
[58] Field of Search ........................... 604/358–363, 604/370

[56] References Cited

U.S. PATENT DOCUMENTS

| | | | |
|---|---|---|---|
| 2,024,145 | 12/1935 | Cline | 167/84 |
| 2,940,449 | 6/1960 | Thomson | 604/359 |
| 3,340,875 | 9/1967 | Dudley et al. | 128/290 |
| 3,871,993 | 3/1975 | Morrison | 208/135 |
| 3,939,838 | 2/1976 | Fujinami et al. | 128/290 R |
| 3,995,636 | 12/1976 | Murray et al. | 128/285 |
| 4,055,184 | 10/1977 | Karami | 128/287 |
| 4,186,743 | 2/1980 | Steiger | 128/284 |
| 4,226,237 | 10/1980 | Levesque | 128/285 |
| 4,304,675 | 12/1981 | Corey et al. | 252/8.6 |
| 4,372,309 | 2/1983 | Fowler | 128/284 |
| 4,505,705 | 3/1985 | Matthews et al. | 604/385 |
| 4,534,962 | 8/1985 | Marschner | 424/65 |
| 4,545,080 | 10/1985 | Gorham | 2/54 |
| 4,547,195 | 10/1985 | Jackson | 604/359 |
| 4,583,980 | 4/1986 | Schneider et al. | 604/359 |
| 4,826,497 | 5/1989 | Marcus et al. | 604/359 |
| 5,019,062 | 5/1991 | Ryan et al. | 604/359 |

FOREIGN PATENT DOCUMENTS 109904 2/1939 Australia .
WO8101643 6/1981 World Int. Prop. O. .

Primary Examiner—Randall L. Green
Assistant Examiner—Rob Clarke
Attorney, Agent, or Firm—Thomas J. Connelly

[57] ABSTRACT

An absorbent article is disclosed for absorbing and retaining human exudate. The article includes an absorbent having a first surface facing the body of a user and a second surface aligned approximately opposite to the first surface. A liquid-impermeable baffle is positioned adjacent to at least the second surface of the absorbent while a fluid-permeable cover is positioned adjacent to at least the first surface of the absorbent. A deodorizing mixture is positioned within the article and is positioned to remain dry for a substantial period of time. The mixture is an anhydrous, non-buffer blend of at least basic and pH neutral odor absorbing particles.

15 Claims, 5 Drawing Sheets

ABSORBENT ARTICLE CONTAINING AN ANHYDROUS DEODORANT

This application is a file wrapper continuation of U.S. Ser. No. 685,363, filed Apr. 15, 1991, now abandoned, which in turn is a continuation-in-part of U.S. Ser. No. 428,085 filed Oct. 27, 1989, now issued as U.S. Pat. No. 5,037,412, which in turn is a continuation-in-part of U.S. Ser. No. 354,337, filed May 23, 1989, now abandoned, which in turn is a continuation-in-part of U.S. Ser. No. 213,399, filed Jun. 30, 1988 now abandoned.

FIELD OF THE INVENTION

This invention relates to an absorbent article, such as a diaper, feminine pad, panty liner, incontinent garment, underarm shield, or bed pad, which contains an anhydrous deodorant mixture including basic and pH neutral odor absorbing particles. More specifically, the mixture is a non-buffer.

BACKGROUND OF THE INVENTION

Absorbent articles designed to be worn by humans to absorb a quantity of fluid, for example: urine, menstrual fluid, perspiration, etc., are known to acquire a variety of malodorous compounds including amines and fatty acids. The emanation of odors from these absorbent articles can cause the user to feel self-conscious. Furthermore, an absorbent article may emit an odor immediately after receiving the initial flow of body fluid, which is well before the absorbent article has retained a significant amount of fluid for which it has capacity. In such a situation, the user may not prefer to change the product due to its cost, time of occurrence or other consideration, yet would like to eliminate the malodor.

A number of prior art devices have attempted to mask the malodor or to camouflage it with an artificial scent, such as perfume. U.S. Pat. Nos. 4,547,195, 4,545,080, 4,186,743 and 3,939,838 are examples of such prior art. In addition, there are patents which teach specific deodorant compositions for controlling malodors in feminine napkins and wound dressings. U.S. Pat. Nos. 2,024,145, 3,871,993 and 3,995,636 and Australia patent 109,904 are examples of different types of deodorants.

For absorbent articles designed for absorbing urine and menstrual fluid, it is known that such body fluids contain acidic, basic and pH neutral odors which can best be controlled by providing a deodorant which has an acidic, basic and pH neutral odor absorbing properties. However, until now manufacturers have concentrated on formulating deodorants with acid and base buffers which are activated when wetted by body fluid. World patent 81/01643 is one such patent which teaches the use of ion exchange materials for the deodorant. Other references, such as U.S. Pat. Nos. 4,372,309, 4,583,980, 4,055,184 and 3,340,875, describe controlling volatile nitrogen compounds, using citric acid or acetyl citric acid to control basic odors, and using hydrolyzed starch polyacrylonitrile graft copolymers in acidic form. However, in the above references the deodorant has to be wetted before the buffer compound starts to control the malodor.

Still other U.S. patents, such as U.S. Pat. Nos. 4,304,675; 4,534,962 and 4,826,497, teach deodorizing compositions for rugs and catamenial devices. The compositions vary, but the use of sodium or potassium bicarbonate and natural and synthetic zeolites are disclosed.

While the above-identified teachings attempt to alleviate malodors emanating from absorbent articles, there is still a need for a deodorant which can handle various types of malodors while in the dry state.

SUMMARY OF THE INVENTION

Briefly, the present invention relates to an absorbent article, such as a diaper, a feminine pad, a panty liner, an incontinent garment, an underarm shield, a bed pad, etc., which contains an anhydrous deodorant. The article consists of an absorbent having a first surface facing the body of a user and a second surface aligned approximately opposite to the first surface. A liquid-impermeable baffle is positioned adjacent to at least the second surface of the absorbent, while a fluid-permeable cover is positioned adjacent to at least the first surface of the absorbent. A deodorant for absorbing malodors emanating from the absorbent is positioned within the article and is designed to function in a dry state. That is, the deodorant ingredients do not function as a buffer and do not have to be wetted in order to absorb malodors. The deodorant is a non-buffer, anhydrous mixture of at least basic and pH neutral odor absorbing particles. The deodorant is preferably positioned around the outer perimeter or edges of the article, such that it will remain dry and absorb odors for a longer period of time.

The general object of this invention is to provide an absorbent article with an anhydrous deodorant. A more specific object of this invention is to provide a deodorant mixture which is a non-buffer.

Another object of this invention is to provide an absorbent article with a deodorant mixture containing at least basic and pH neutral odor absorbing particles which are dispersed around the outer perimeter of the article between the absorbent and the liquid-impermeable baffle.

Still, another object of this invention is to provide an absorbent article which contains a vapor-permeable member positioned between the absorbent and the liquid-impermeable baffle and the deodorant is positioned below the vapor-permeable member.

Still further, an object of this invention is to provide a low cost, easily manufactured absorbent article which contains an anhydrous deodorant for controlling malodors emitting from the article during use.

Still further, another object of this invention is to provide a feminine pad or panty liner with a deodorant which can operate without being wetted.

Other objects and advantages of the present invention will become more apparent to those skilled in the art in view of the following description and the accompanying drawings.

DETAILED DESCRIPTION OF THE PREFERRED EMBODIMENT

Figure 1:
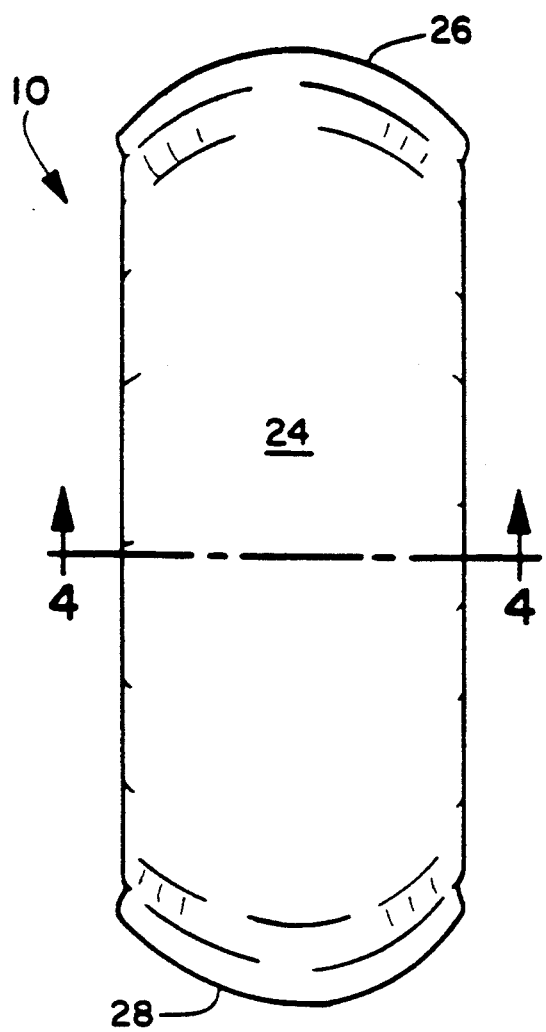
FIG. 1 is a top view of an absorbent article, such as a feminine pad, containing a deodorant mixture for absorbing odors.
Figure 2:
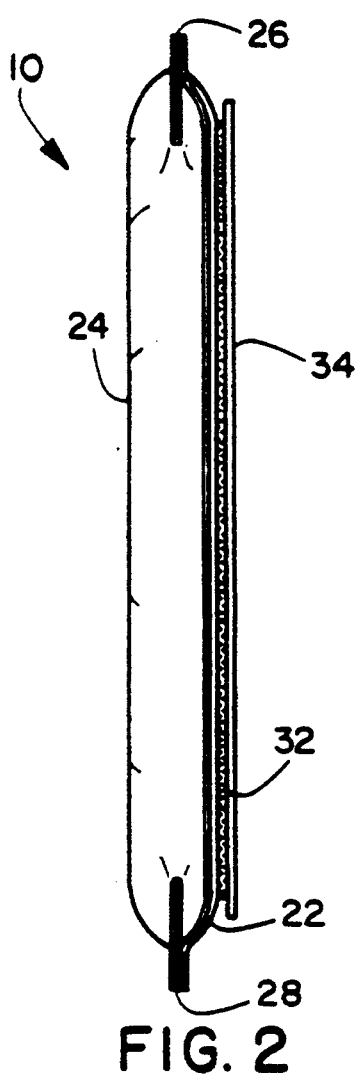
FIG. 2 is a side view of the absorbent article shown in FIG. 1.
Figure 3:
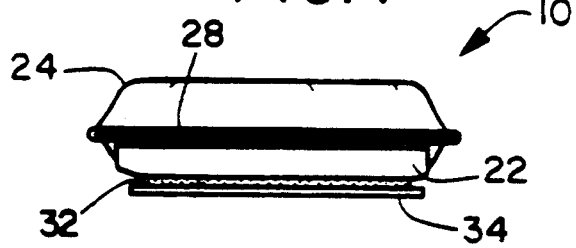
FIG. 3 is an end view of the absorbent article shown in FIG. 1.

Referring to FIGS. 1-4, an absorbent article 10 is shown. The article 10 can be a diaper, a feminine pad, a panty liner, an incontinent garment, an underarm shield, a bed pad, etc. For purposes of discussion, the absorbent article 10 is depicted as a feminine pad. The absorbent article 10 contains an absorbent 12, best shown in FIG. 4, which can be constructed of cellulose, wood fluff, coform, meltblown or carded material, sphagnum moss, or other conventional material. Coform is an air-formed mixture of melt blown and staple fibers, such as wood fluff. The absorbent 12 is shown C-folded having abutting ends 14 and 16. The absorbent 12 contains a first surface 18, which faces the body of a user, and a second surface 20 aligned approximately opposite to the first surface 18.

Figure 4:
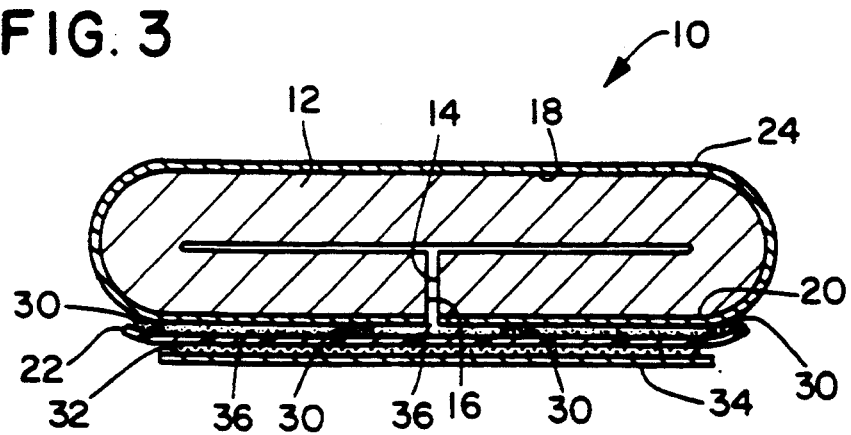
FIG. 4 is an enlarged cross-sectional view of the absorbent article shown in FIG. I taken along line 4—4.

The absorbent article 10 also contains a liquid-impermeable baffle 22, which is positioned adjacent to at least the second surface 20 of the absorbent 12. It is possible that the baffle 22 can extend upwards around a portion of the sides of the absorbent 12 and even overlap a portion of the first surface 18 in certain embodiments. The liquid-impermeable baffle 22 can be constructed of polypropylene, polyethylene or other suitable material. A fluid-permeable cover 24 is positioned adjacent to at least the first surface 18 of the absorbent 12. The cover 24 can extend completely around the absorbent 12, as is shown in FIG. 4. Alternatively, it can partially cover the absorbent 12 and be attached directly to the baffle 22 or an intermediate member, see FIGS. 7 and 8, so that both the cover 24 and the baffle 22 sandwich the absorbent 12 therebetween. The cover 24 can be a nonwoven, spunbonded or film material, or be made from a material having a netting type texture. The cover 24 can be porous, embossed, perforated or exhibit a smooth surface. The cover 24 is designed to come in contact with the body of the user and present a soft and comfortable feel while exhibiting the ability to allow human exudate in the form of blood, menses, urine or other types of body fluid to readily pass through into the absorbent 12.

When the cover 24 completely surrounds the absorbent 12, as is shown in FIG. 4, opposite ends 26 and 28 of the cover 24 can be bonded together. Furthermore, the baffle 22 can be bonded to the outside surface of the cover 24 by construction adhesive 30. In FIG. 4, four distally spaced longitudinal strips of construction adhesive 30 secure the baffle 22 to the cover 24. It is possible to use only a single strip of adhesive, if one desires. As with most conventional pads, a garment adhesive 32, which can be pressure sensitive, is applied to an outside surface of the baffle 22 and a removable peel strip 34 is attached thereto. The peel strip 34 is designed to be removed just prior to use of the product by the ultimate consumer. In use, the consumer removes the peel strip 34 and attaches the product to the inside surface of an undergarment so that the product will remain in position relative to the perineum of the body.

The absorbent article 10 also contains a deodorizing mixture 36 for absorbing malodors which may emanate therefrom during use. The odors are introduced into the absorbent article 10 when the absorbent 12 absorbs body fluids.

Various bodily fluids contain malodorous chemical compounds including acyclic and cyclic amines, aldehydes, fatty acids, and sulfur-containing compounds such as sulfides. Vaginal secretions and used menstrual pads may contain many malodorous chemical compounds; for example, trimethyl amine, pyridine, furaldehye, isovaleric acid, and methyl mercaptan. The boiling points of these compounds are 3° C., 115° C., 162° C., 179° C., and 37° C., respectively. To facilitate laboratory evaluations, five compounds with boiling points significantly above room temperature were chosen as models to represent five types of chemical compounds. Triethyl amine (boiling point 89° C.), pyridine, furaldehyde, isovaleric acid, and n-propyl sulfide (boiling point 142° C.) were chosen as representatives of the types of odoriferous chemical compounds to which an absorbent article might be exposed.

The particular malodorous compounds, which will be absorbed by various absorbent articles, will vary depending upon the person who is wearing the absorbent article and the type of fluid absorbed; i.e., urine, menstrual fluid, perspiration, milk, etc. For feminine pads, the length of time that the article is worn, the quantity of fluid which is absorbed, and the exposure of the pad to different bodily fluids will determine which odors can be emitted by the absorbent article.

The deodorizing mixture 36 is an anhydrous mixture of basic and pH neutral odor absorbing particles and may also include acidic odor absorbing particles. The mixture is a non-buffer which neutralizes odors emanating from the article 10. The particles are mixed together, but each particle maintains its distinct identity. Each particle is anhydrous and does not contain water either absorbed on its surface or combined as water of crystallization. All the particles are dry during the assembly process and are designed to remove odors in the dry state and are not normally designed to be wetted. Because of this, the particles do not act as a buffer and do not require contact by urine or menstrual fluid before they start to take effect. The particles are dry blended and mixed without the use of solvent or water and are retained in the dry state throughout the manufacturing process. The particles themselves do not emit an unpleasant odor. The deodorizing mixture 36 is blended without the addition of a solvent or water which is contrary to most buffers which are blended with the addition of a solvent or with water.

As mentioned above, the deodorizing mixture 36 can contain acidic, basic and pH neutral odor absorbing particles. The acidic particles, those having a pH of less than 7, may be any suitable dry acid material which will provide control of basic odoriferous compounds. Typical of such materials are ascorbic acid, stearic acid, boric acid, maleic acid polymers, malonic acid, maleic acid, polyacrylic acid and monopotassium phosphate. A preferred material is citric acid, for it is low in cost, safe to use, and has a low equivalent weight. Low equivalent weight means that a large amount of the acid is present per unit of weight. The amount of acid present will vary depending upon the type of product that it is incorporated into and the particular odors that it is designed to control. For feminine products, it has been found that very small amounts of acid, less than about 10 percent, preferably less than about 5 percent, and most preferably less than about 1 percent of the total weight of the deodorizing mixture is desirous. It should be noted that the acid component can be eliminated if desired. The amount of acid should be less than, or approximately equal to, the stoichiometric balance of the basic compound. A value equal to the stoichiometric balance is desirable, as the effectiveness of the acid and base should be exhausted at approximately the same time.

The basic odor controlling particles of the deodorizing mixture 36, those having a pH of greater than 7, are to control acidic odoriferous compounds. Typical of such basic odor control particles are inorganic salts of carbonates, bicarbonate, phosphate, biphosphate, sulfate, bisulfate and mixtures thereof. A preferred basic odor absorbing material is sodium bicarbonate, because it is low in cost, safe to use, and its effectiveness has been established over a number of years by previous use in consumer products. The amount of the basic odor absorbing particles used in the blend can be between about 25 and 99 percent of the total weight of the deodorizing mixture. A preferred range is between about 75 and 95 percent of the total weight of the deodorizing mixture. These percentages will give adequate odor control and will also provide the stoichiometric balance as discussed above.

The pH neutral odor absorbing particles of the deodorizing mixture 36, those having a pH of approximately 7, are designed to absorb odoriferous compounds which are not acidic or basic. Typical of such pH neutral odor absorbing materials are activated carbon, clays, silicas, diatomaceous earth, polystyrene derivatives, zeolites, molecular sieves and starches. A preferred material is a synthetic molecular sieve, such as synthetic sodium aluminum silicate with a zeolite structure that has been treated to be absorptive of odoriferous compounds. Such material is commercially available from UOP as ABSCENTS® and SMELLRITE®. It should be noted that, in the presence of water vapor, conventional molecular sieves tend to loose most of their capacity to absorb odors. In contrast, ABSCENTS® and SMELLRITE® appear to retain most of their absorbent capacity in moist conditions and are, therefore, preferred. The amount of the pH neutral odor absorbing particles used in the blend can be between about 1 to 25 percent of the total weight of the deodorizing mixture. A preferred range is between about 10 to 20 percent, and a most preferred range is between 15 to 20 percent of the total weight of the deodorizing mixture.

As stated above, the deodorizing mixture 36 is a non-buffer mixture which can be inserted into an absorbent article in a variety of ways. Preferably, the deodorizing mixture 36 will be positioned such that it will not be immediately contacted by body fluids discharged by the user. The non-buffered mixture is most effective when dry, although it will work in the wet condition. The deodorizing mixture 36 should be positioned within the absorbent article so as to intersect vapors emanating from the article and, thereby, absorb the malodors. In this regard, the deodorizing mixture 36 appears to be very useful when located around the peripheral edge, near the lateral sides of the article, or on the second surface 20 of the absorbent 12. In all of these positions, the deodorizing mixture 36 will remain dry until the absorbent article has absorbed a significant amount of fluid relative to its ultimate capacity. It is also possible to position the deodorizing mixture 36 in a central portion of the product, but shield it by hydrophobic fibers in order to minimize its contact by body fluid while still allowing it to absorb malodors. The deodorizing mixture 36 can further be placed within a fibrous material that is hydrophobic in order to discourage passage of fluid therethrough.

It should be noted that the deodorizing mixture 36 absorbs the malodors emanating from the article 10, and this differs from fragrances which are designed to conceal or mask odors. If one wished to add a perfume or a scent to the deodorizing mixture 36, one must carefully select the perfume or scent to avoid detracting from the functional ability of the mixture itself. The present deodorizing mixture 36, being anhydrous, exhibits good shelf life and stability and does not require any special type of packaging or handling. However, to maintain maximum effectiveness, it is advantageous to avoid close contact with strongly scented materials during extended storage.

Figure 5:
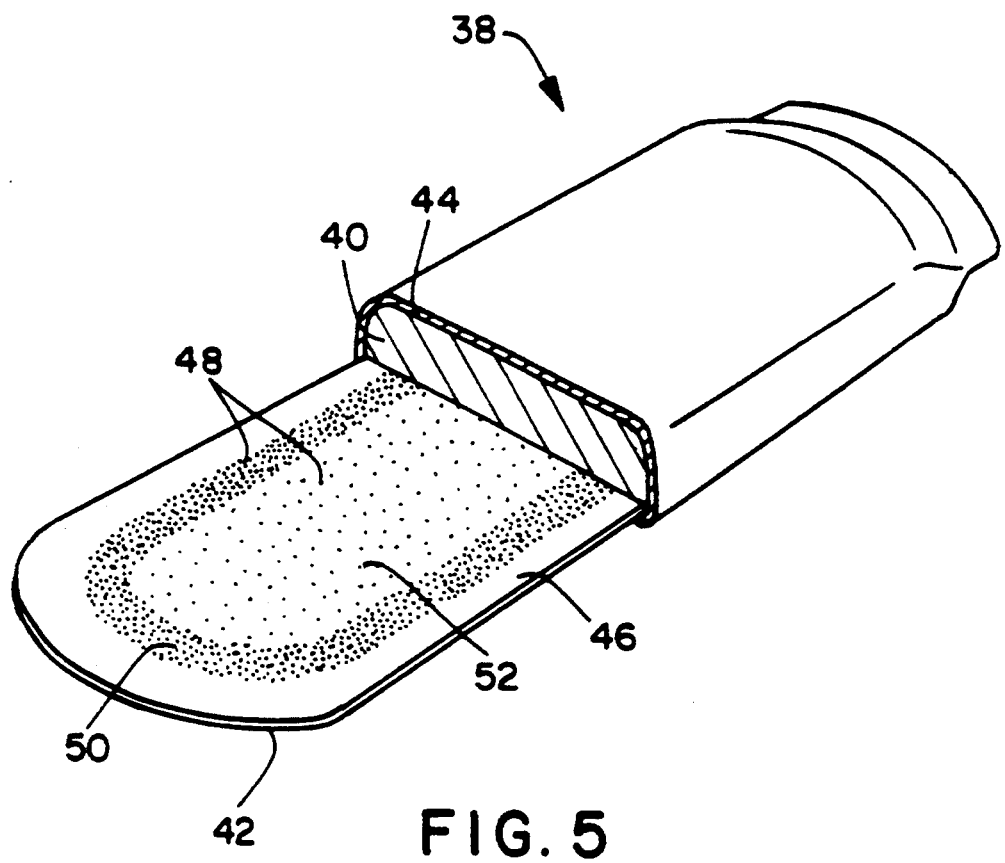
FIG. 5 is a perspective view of an absorbent article showing a majority of the deodorant mixture positioned adjacent to the outer periphery of the article between the absorbent and the liquid-impermeable baffle.

Referring to FIG. 5, an absorbent article 38 is shown having an absorbent 40 and a liquid-impermeable baffle 42 surrounded by a fluid-permeable cover 44. The baffle 42 has an upper surface 46 which is in contact with a lower surface of the absorbent 40. Positioned on the upper surface 46 is a deodorizing mixture 48 which can contain basic and pH neutral odor absorbing particles, as well as acidic particles, if desired. The deodorizing mixture 48 is applied to the surface 46 such that a greater quantity or amount of the mixture is present about the outer periphery of the baffle 42 than is present in the central portion thereof. The greater number of particles, designated 50, are shown being more compact and located closer together. The lesser number of particles, designated 52, are located in the central portion and are spaced a greater distance apart. The novel feature of utilizing a greater quantity of the particles around the outer periphery of the absorbent article 38 allows the deodorizing mixture 48 to remain drier for a longer period of time and, therefore, will facilitate better absorption of malodors.

It has been found that the particle size of the deodorizing mixture is important, especially when one attempts to form a blend or mixture. If any one of the ingredients is overly large, or particularly small, it is possible that, during normal shipping or stacking of the product, the particles will shift and separate. This can cause a substantial amount of one of the particles to end up on the bottom, while other particles will be located at the top of the mixture. In order to provide effective odor control, it is important that the mixture remain blended and the particles have a size which will allow them to stay blended. Experimentation has shown that, when the components of the deodorizing mixture are citric acid, sodium bicarbonate and zeolite, the citric acid particles have a size of between about 40 and 400 micrometers, the sodium bicarbonate particles have a size of between about 25 and 250 micrometers and the zeolite particles have a size of less than about 20 micrometers. It should be noted that within the above-identified ranges a substantial amount of the particles should have the stated sizes. If one were to use a sieve measurement to establish size, then the following U.S. standard sieve sizes would correspond to the above-mentioned micrometers. The citric acid should have a size such that more than 90% passes through a number 40 sieve and more than 90% is retained on a number 400 sieve. The sodium bicarbonate should have a size such that more than 90% passes through a number 70 sieve and more than 70% is retained in a number 400 sieve. The zeolite should have a size such that more than 70% passes through a number 400 sieve. Because many zeolites tend to agglomerate, to obtain an accurate measure of the zeolite particle size may require the use of a free flowing, fine particle size material as an aid in driving the zeolite through the sieve.

Another measurement of the amount of the deodorizing mixture which should be present in the absorbent article will depend upon the given purpose that the article is designed to serve. It has been found that from about 5 to 50 percent and preferably about 10 to 25 percent of the total weight of the article should be made up of the mixture. It has also been found that the mixture works satisfactorily when a substantial portion of the mixture is positioned in the outer 50 percent of the total surface area of the article. For products having a weight of at least 2 grams, the amount of the deodorizing mixture 36 can be between 0.15 to 2.5 grams, preferably 0.2 to 2.0 grams, and most preferably between about 0.4 and 1.0 grams. A preferred amount has been found to be about 1 gram for providing adequate odor protection without substantially adding to cost. For a 1 gram mixture, one can have about 75 to 95 percent by weight of sodium bicarbonate and about 5 to 25 percent by weight of a molecular sieve zeolite.

Figure 6:
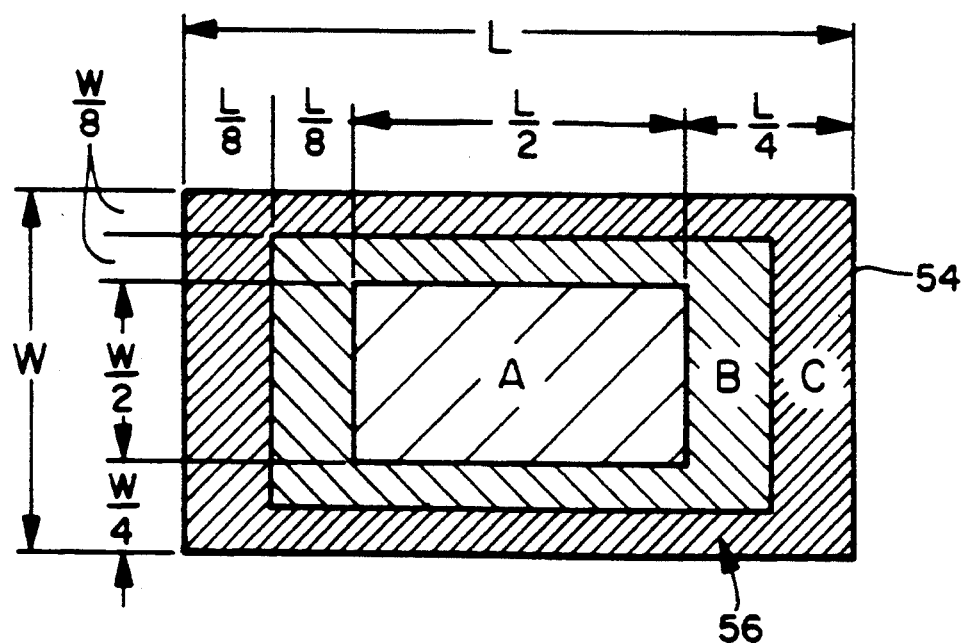
FIG. 6 is a schematic view of a rectangular sheet showing the concentration of a deodorant mixture positioned thereon with "A" being a minimum quantity, "B" being an intermediate quantity and "C" being the greater quantity.

Referring to FIG. 6, a schematic is shown of a rectangular sheet 54 having a quantity of a deodorizing mixture 56 positioned thereon. The rectangular sheet 54 has a length denoted "L" and a width denoted "W". The sheet 54 is representative of the surface of a liquid-impermeable baffle which would receive the deodorizing mixture. The sheet 54 contains three areas designated "A", "B" and "C" with the central portion labeled "A", the intermediate portion labeled "B", and the extreme outer portion labeled "C". The amount of the deodorizing mixture 56 present in each portion varies. The minimum amount of the mixture 56 is positioned in area "A", an intermediate amount is positioned in area "B", and the maximum amount is positioned in area "C". Experimentation has shown that at least 50 percent and preferably 75 percent of the deodorizing mixture 56 should be located in the outer 50 percent of the total surface area of the absorbent article. More preferably, at least the outer 75 percent of the deodorizing mixture 56 should be located in the outer 75 percent of the total surface area of the absorbent article. An optimum absorbent article would have at least 90 percent of the deodorizing mixture 56 located in the outer 75 percent of the total surface area of the article. The purpose for positioning a greater quantity of the deodorizing mixture 56 adjacent to the perimeter of the sheet 54 is to allow it to maintain its dryness for a longer period of time and to be in a position to intercept the odors emanating from the product along the sides and bottom surfaces. By positioning the deodorizing mixture between the absorbent and the liquid-impermeable baffle, as is shown in FIG. 5, the deodorizing mixture will be spaced away from the porous fluid-permeable cover. This distant relationship will assist in preventing the mixture from migrating up and out through the cover and into contact with the body of the user. Although the mixture 56 is not known to be harmful to the skin, it would be preferable to keep the mixture away from the skin. One reason for this is that consumers have expressed their dislike with having a residue of powder left on their body after using an absorbent article.

Figure 7:
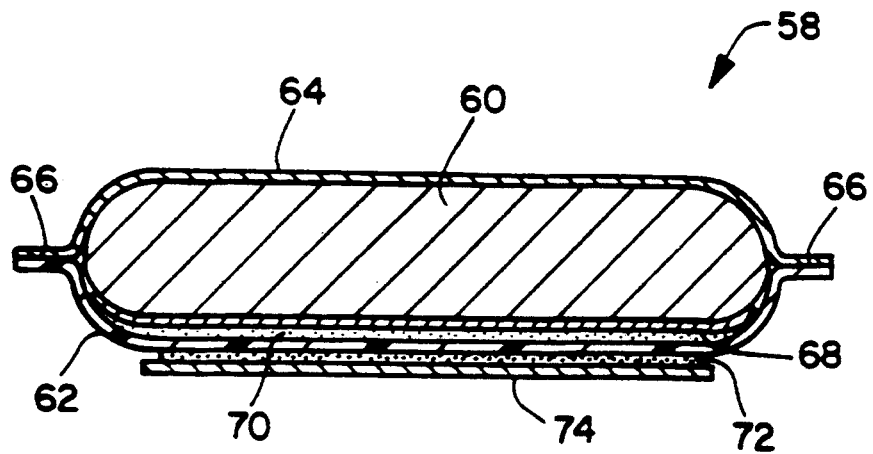
FIG. 7 is a cross-sectional view of an absorbent article having a deodorant mixture positioned between a vapor-permeable layer and a liquid-impermeable baffle.

Referring to FIG. 7, an absorbent article 58 is shown having an absorbent 60 sandwiched between a liquid-impermeable baffle 62 and a fluid-permeable cover 64. The baffle 62 and cover 64 are bonded together, such as by an adhesive or ultrasonic sealing, to form a peripheral seal 66. The absorbent article 58 also contains a vapor-permeable member or layer 68 which is positioned between the absorbent 60 and the liquid-impermeable baffle 62. The vapor-permeable member 68 can be a nonwoven, fibrous web which is preferably liquid impermeable. The vapor-permeable member 68 can be bonded to the absorbent 60, the baffle 62, or both, such as by a construction adhesive or by heat. Preferably, the vapor-permeable member 68 is located adjacent to the surface of the absorbent 60 which is away from the body of the user. Alternatively, the vapor-permeable member 68 can simply be positioned adjacent to the absorbent 60 without actually being bonding to it. The vapor-permeable member 68 can optionally be liquid permeable but should contain some of the hydrophobic fibers so as to reduce the amount of liquids which will permeate therethrough. It should also be noted that the vapor-permeable member 68 can have a smaller surface area than that of the liquid-impermeable baffle 62 such that less material has to be used. This may be important if the vapor-permeable material 68 is very costly. Positioned between the vapor-permeable member 68 and the liquid-impermeable baffle 62 is a deodorizing mixture 70 as taught above. The vapor-permeable member 68 will allow the malodors from the absorbent 60 to emanate therethrough and be absorbed by the deodorizing mixture 70 while providing a barrier which will prolong the amount of time it takes before the deodorizing mixture 70 is wetted. As mentioned above, the deodorizing mixture 70 is a non-buffer and, therefore, is not designed to be wetted in order to activate it. The absorbent article 58 also contains a garment adhesive 72 and a peel strip 74, the purpose of which was explained above.

Figure 8:
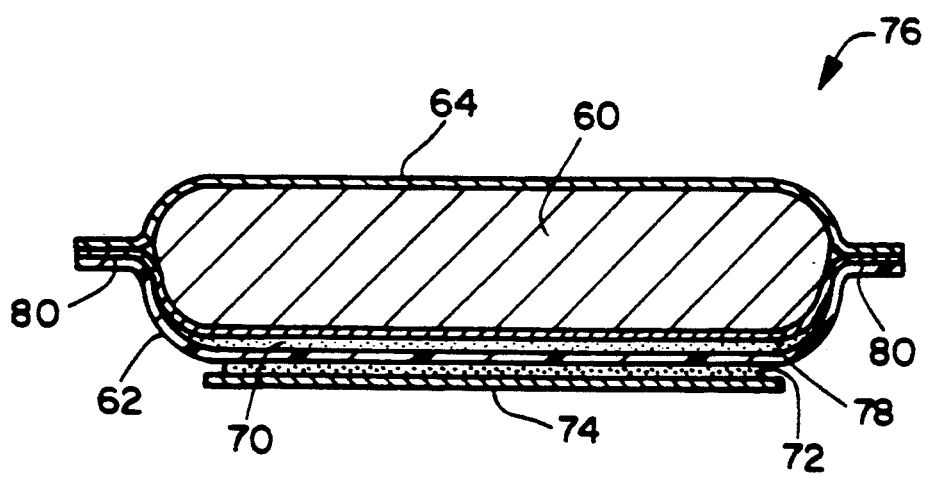
FIG. 8 is a cross-sectional view of an absorbent article showing a deodorant mixture positioned between a vapor-permeable layer and a liquid-impermeable baffle wherein both the vapor-permeable layer and the liquid-impermeable baffle have approximately equal surface areas.

Referring to FIG. 8, an alternative absorbent article 76 is shown which is similar to the absorbent article 58. All of the structural features, which are identical to those discussed above for FIG. 7, bear the same reference numerical. The only difference is that, in FIG. 8, a vapor-permeable member or layer 78 is coterminous with the baffle 62 and the cover 64 and is joined with both to form a peripheral seal 80. It should be noted that the deodorizing mixture can be deposited onto the baffle by gravity, be sprinkled on, be blown on, be air-formed, or be mixed with a nonaqueous binder to form a layer. The layer is then interwoven or meltblown onto a substrate. The particular method of introducing the deodorizing mixture into the product will depend upon the equipment available, the amount of mixture to be applied, the location where the mixture is to be applied, the type of product, etc.

Figure 9:
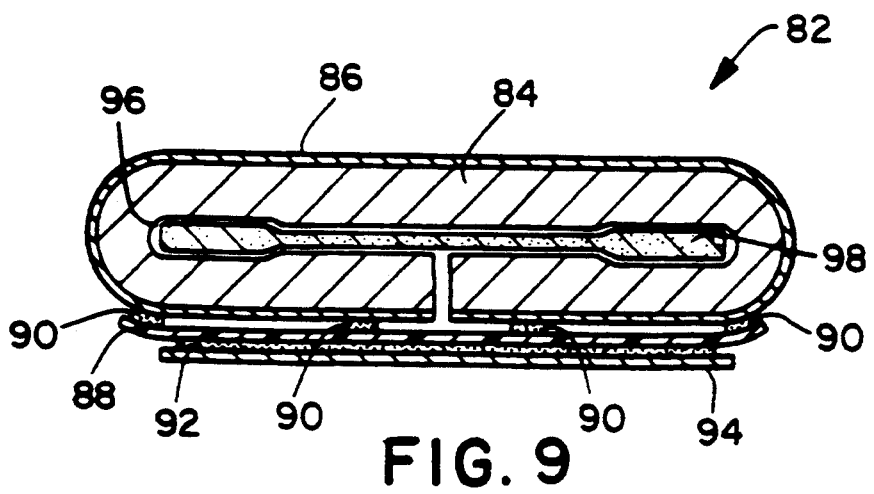
FIG. 9 is a cross-sectional view of an absorbent article having a non-uniform layer of a deodorant mixture positioned within the absorbent, such that a greater quantity of the deodorant mixture is adjacent to the outer periphery of the article and a lesser amount of the mixture is positioned in the center of the article.

Referring to FIG. 9, another embodiment of an absorbent article 82 is shown having an absorbent 84 completely surrounded by a fluid-permeable cover 86. A liquid-impermeable baffle 88 is bonded by several strips of construction adhesive 90 to the exterior of the cover 86 on the side away from the body of the user. The absorbent article 82 also contains a garment adhesive 92 covered by a removable peel strip 94, the purpose of which was explained above. The unique feature of the absorbent article 82 is that the absorbent 84 is C-folded and has a cavity or opening 96 located within the horizontal center portion of the C-fold. Positioned within the cavity 96 is a nonwoven web 98 made up of a deodorizing mixture of at least basic and pH neutral odor absorbing particles. The nonwoven web 98 has a reduced diameter in the center, such that the outer periphery of the web 98 is thicker than the central portion. The web 98 can be formed by dry mixing and blending the different components and then adding a nonaqueous binder to hold the particles together. The web 98 can be compressed to a desired cross-sectional configuration. The web 98 is then simply laid onto the absorbent 84 before it is C-folded into the final product. The web 98 can also contain hydrophobic fibers, if desired, to add strength and integrity as well as to repel fluid or moisture from contacting the odor absorbing particles.

Figure 10:
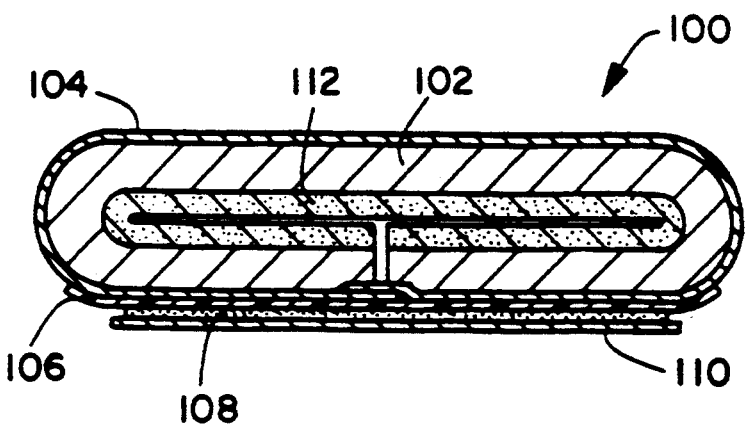
FIG. 10 is a cross-sectional view of an alternative embodiment showing a C-folded layer of deodorant positioned within the absorbent.

Referring to FIG. 10, an absorbent article 100 is shown having a C-folded absorbent 102 completely surrounded by a fluid-permeable cover 104. A liquid-impermeable baffle 106 is bonded to an exterior surface of the cover which is spaced away from the body of the user. A garment adhesive 108 is bonded to an exterior surface of the baffle 106 and is covered by a peel strip 110. A nonwoven web 112, constructed of a deodorizing mixture of at least basic and pH neutral odor absorbing particles, is C-folded within the center portion of the absorbent 102. The web 112 is shown having a constant thickness and, again, may contain hydrophobic fibers if desired.

Figure 11:
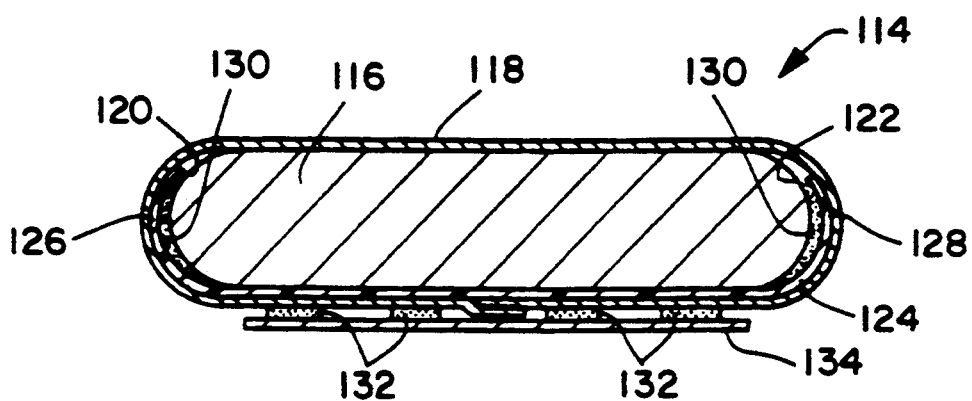
FIG. 11 is another embodiment of an absorbent article having a liquid-impermeable baffle extending upwards about the sides of the absorbent, and a deodorant mixture is positioned between the sides of the absorbent and the interior surface of the liquid-impermeable baffle.

Referring to FIG. 11, another embodiment of an absorbent article 114 is depicted having an absorbent 116 which is completely surrounded by a fluid-permeable cover 118. The absorbent 116 contains a pair of opposed side surfaces 120 and 122. A liquid-impermeable baffle 124, having a pair of upwardly extending side portions 126 and 128, is positioned between the absorbent 116 and the cover 118. The side portions 126 and 128 extend upward and substantially cover a greater portion of the side surfaces 120 and 122. Positioned in the cavities or spaces between the surfaces 120 and 126, and the surfaces 122 and 128, respectively, is a deodorizing mixture 130. The absorbent article 114 also contains one or more garment adhesive strips 132 which are bonded to an exterior surface of the cover 118 and which hold a removable peel strip 134 in place.

The deodorizing mixture 130 is composed of at least basic and pH neutral odor absorbing particles. By positioning the deodorizing mixture 130 on the sides or peripheral portions of the absorbent article 114, one can be assured that the deodorizing mixture 130 will absorb any malodors emanating from the side or periphery while remaining dry for a greater portion of the life of the product. The reason for this is that, in most absorbent articles, the fluid is dispersed along the central longitudinal top portion of the cover and is drawn down into the absorbent along the central vertical "Y" axis. As the absorbent 116 absorbs and retains additional fluid, the fluid slowly progresses outward along the "X" and "Z" axes wetting more of the absorbent 116. The absorbent article 114 can absorb roughly 75 percent of the total fluid which it is designed to absorb before the outer periphery or side edges will be contacted by the fluid.

Figure 12:
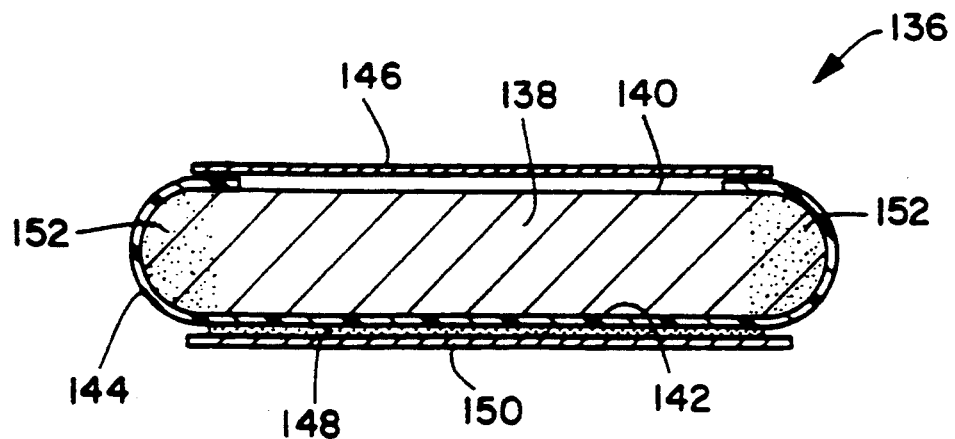
FIG. 12 is a cross-sectional view of another embodiment showing a deodorant mixture incorporated into the outer peripheral surface of the absorbent article.

Referring to FIG. 12, another embodiment of an absorbent article 136 is shown containing an absorbent 138 having a first surface 140 facing the body of a user and a second surface 142 positioned away from the body of the user. A liquid-impermeable baffle 144 is positioned adjacent to the second surface 142 and wraps around the sides of the absorbent 138 and partially covers a portion of the first surface 140. Bonded to the baffle 144 and positioned adjacent to the first surface 140 of the absorbent 138 is a fluid-permeable cover 146. A garment adhesive 148 is applied to the exterior surface of the baffle 144 and is covered by a removable peel strip 150. A deodorizing mixture 152 is incorporated into the absorbent 138 and extends about the entire periphery thereof. The deodorizing mixture 152 can extend inward from the lateral side edges of the absorbent 138 approximately 10 to 25 percent of its total width. By incorporating the deodorizing mixture 152 into the side edges or periphery of the absorbent 138, one may be able to speed up the manufacturing process and provide a location for the deodorizing mixture 152 which will maintain its dryness for essentially the entire life of the product.

Figure 13:
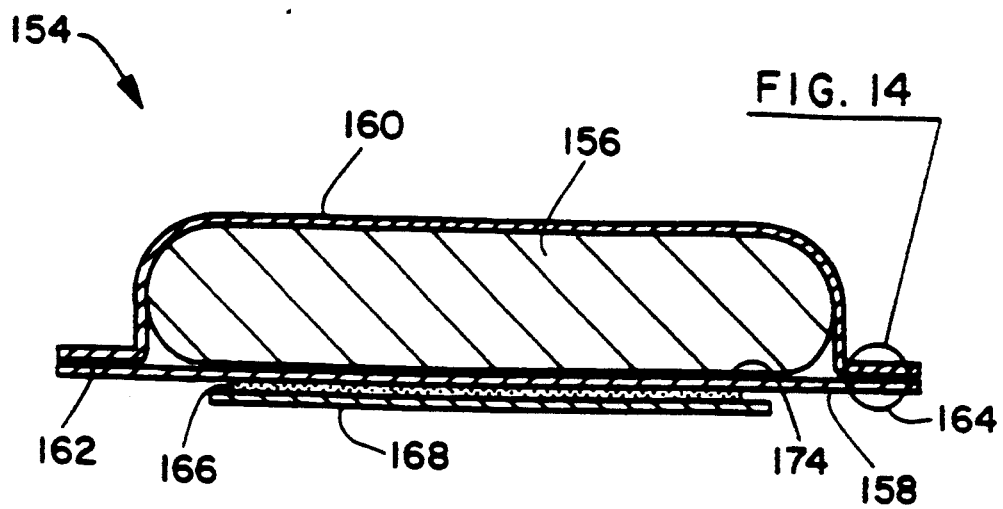
FIG. 13 is a cross-sectional view of another embodiment showing a deodorant mixture incorporated into the liquid-impermeable baffle.
Figure 14:
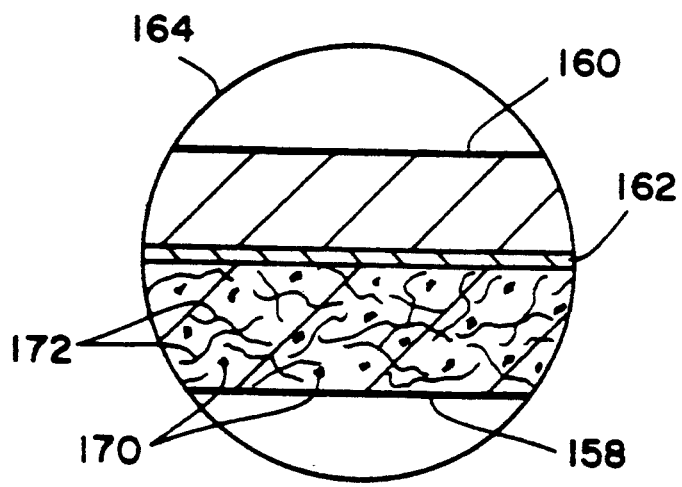
FIG. 14 is an enlarged view of the circled area shown in FIG. 13 depicting the deodorant particles dispersed between fibers of the liquid-impermeable baffle.

Referring to FIGS. 13 and 14, another embodiment of an absorbent article 154 is shown having an absorbent 156 sandwiched between a liquid-impermeable baffle 158 and a fluid-permeable cover 160. The baffle 158 and the cover 160 are joined together about their periphery by construction adhesive 162 to form a peripheral seal 164. The absorbent article 154 also contains a garment adhesive 166 applied to an exterior surface of the baffle 158 which is covered by a removable peel strip 168. The novel feature of the absorbent article 154 is that deodorizing particles 170 are incorporated and dispersed within the baffle 158. The baffle 158 can also contain fibrous materials 172 which can provide integrity as well as acting as a carrier for the deodorizing particles 170. The deodorizing particles 170 are individual basic and pH neutral odor absorbing particles blended or mixed together. Since the deodorizing particles 170 are dispersed and incorporated directly into the baffle 158, the baffle 158 should be vapor permeable. By being vapor permeable, yet liquid impermeable, the baffle 158 will allow odors to emanate therethrough while preventing liquid from exiting the article 154.

Referring once again to FIG. 13, it should be noted that a construction adhesive 174 is applied between the lower surface of the absorbent 156 and the inner surface of the baffle 158. The adhesive 174 will bond the baffle 158 and provide integrity to the product. The presence of the adhesive 174 is optional and can be eliminated if not needed.

An illustrated laboratory test was conducted which, although not totally reflective of real world conditions, does offer evidence supporting the contention that the deodorizing mixture described herein is more effective than the presence of a single absorbing substance, such as only an acid absorbent or a base absorbent. The odoriferous compounds given off by absorbent articles, particularly menstrual pads and panty liners, vary with the particular person utilizing the pad as well as the phase of menstrual cycle and the length of time the product is worn. Therefore, exact comparison in real world situations are difficult to document except by numerically calculated preferences in large groups of wearers. However, the effectiveness of the mixture ingredient against the types of odoriferous compounds given off from menstrual products is demonstrated.

EXAMPLE 1

In this example, about 97.5 milligrams (mg) of citric acid, about 127 mg of sodium bicarbonate and about 25 mg of SMELLRITE® molecular sieve material were tested individually and in combination. The particles were exposed to triethyl amine, isovaleric acid, pyridine, furaldehyde, and n-propyl sulfide which were chosen as representative of the types of odoriferous chemical compounds to which an absorbent article might be exposed. A mixture of these compounds was injected onto the particles contained in a sealed vial. A sample of the air above the particles was taken four (4) hours later and analyzed using gas chromatography. The data indicated that the three component mixture was a more effective absorbent overall than any one of the individual components.

TABLE 1

PERCENT (%) REDUCTION OF ODOR LEVEL AFTER FIVE HOURS

| Odorous Compound | Acidic Ab- sorbent | Basic Ab- sorbent | pH Neutral Ab- sorbent | Deo- dorant Mix- ture | Con- trol |
|---|---|---|---|---|---|
| | Citric Acid | Sodium Bicar- bonate | SMELL- RITE ™ | Mix- ture of these 3 sub- stan- ces. | Empty vial |
| | (97.5 mg) | (127.5 mg) | (25 mg) | (250 mg) | |
| Triethyl amine | 98 | 9 | 41 | 97 | 0 |
| Pyridine | 94 | −16 | 33 | 76 | 0 |
| Furaldehyde | −11 | 19 | 56 | 68 | 0 |
| Isovaleric acid | −352 | 56 | −247 | −77 | 0 |
| n-Propyl sulfide | −20 | −22 | 33 | 35 | 0 |
| mean = | −38 | 9 | −17 | 40 | 0 |

Note:
Percent reduction less than zero (0) indicates an odor increase relative to Control.

The effectiveness of the deodorizing mixture was demonstrated in a clinical study. NEW FREEDOM® ANYDAY® pantiliner pads, having a construction similar to that shown in FIG. 4, were tested with a deodorizing mixture in the amount of 1 gram per product. The mixture was evaluated to determine odor reducing ability. Four trained judges evaluated the odor of the products using a 0 to 10 scale.

Thirty-three subjects wore both unscented control products and deodorized test products on alternate days. The judges observed that for twenty of the subjects the deodorized test products had less odor, while for ten subjects the control product had less odor. For three subjects no difference was observed in the odor level between the two products. Table 2 indicates the recorded data.

TABLE 2

| | Clinical Study | |
|---|---|---|
| Difference in mean odor ratings* | Number of Subjects | Observations |
| 2.00 | 1 | Deodorized test |
| 1.75 | 1 | product had less |
| 1.50 | 4 | odor than the |
| 1.25 | 4 | control product. |
| 1.00 | 1 | |
| 0.75 | 5 | |
| 0.50 | 2 | |
| 0.25 | 1 | |
| −0.25 | 8 | Control product had |
| −0.50 | 1 | less odor than |
| −0.75 | 1 | deodorized test product. |
| 0.00 | 3 | Control product and deodorized test product exhibited equal odor. |

0.55 = mean difference
0.75 = standard deviation
0.13 = standard error
*Odor rating for deodorized test product minus the odor rating for control product.

While the invention has been described in conjunction with several specific embodiments, it is to be understood that many alternatives, modifications and variations will be apparent to those skilled in the art in light of the a foregoing description. Accordingly, this invention is intended to embrace all such alternatives, modifications and variations which fall within the spirit and scope of the appended claims.

We claim:

1. An absorbent article comprising;
   a) an absorbent having a first surface and a second surface aligned approximately opposite to said first surface;
   b) a liquid-impermeable baffle positioned adjacent to at least said second surface of said absorbent;
   c) a fluid-permeable cover positioned adjacent to at least said first surface of said absorbent; and
   d) deodorizing means for absorbing malodors emanating from said absorbent, said deodorizing means being an anhydrous mixture of odor absorbing particles including basic odor absorbing particles in the form of sodium bicarbonate and pH neutral odor absorbing particles in the form of a zeolite wherein a substantial amount of said sodium bicarboante particles have a size of between about 25 and 250 micrometers and a substantial amount of said zeolite particles have a size of less than about 20 micrometers, and wherein a substantial portion of said mixture is positioned in the outer 50 percent of the total surface area of said article.

2. The absorbent article of claim 1 wherein at leas 75% of said mixture is positioned in the outer 50% of said article between sad absorbent and said baffle.

3. The absorbent article of claim 1 wherein a vapor-permeable member is positioned between said absorbent and said baffle and said mixture is retained between said vapor-permeable member and said baffle.

4. The absorbent article of claim 3 wherein said vapor-permeable member is liquid impermeable.

5. The absorbent article of claim 1 wherein said anhydrous mixture is blended without the addition of a solvent.

6. The absorbent article of claim 1 wherein said anhydrous mixture is blended without water.

7. An absorbent article comprising:
 a) an absorbent having a first surface and a second surface aligned approximately opposite to said first surface;
 b) a liquid-impermeable baffle positioned adjacent to at least said second surface of said absorbent;
 c) a fluid-permeable cover positioned adjacent to at least said first surface of said absorbent; and
 d) deodorizing means for absorbing malodors emanating from said absorbent, said deodorizing means being an anhydrous mixture of odor absorbing particles including basic odor absorbing particles in the form of sodium bicarbonate and pH neutral odor absorbing particles in the form of a zeolite wherein a substantial amount of said sodium bicarbonate particles have a size of between about 25 and 250 micrometers and a substantial amount of said zeolite particles have a size of less than about 20 micrometers, said mixture representing from about 5 to 50 percent of the total weight of said article and wherein a substantial portion of said mixture is positioned in the outer 50 percent of said article.

8. The absorbent article of claim 7 wherein said mixture represents from about 10 to 25 percent of the total weight of said article.

9. The absorbent article of claim 1 wherein said article has a total weight of between about 2–25 grams and said mixture represents from about 10–25% of the total weight of said article.

10. The absorbent article of claim 9 wherein said mixture has a weight of between about 0.4 and 1.0 grams.

11. An absorbent article comprising:
 a) an absorbent having a first surface and a second surface aligned approximately opposite to said first surface;
 b) a liquid-impermeable baffle positioned adjacent to at least said second surface of said absorbent;
 c) a fluid-permeable cover positioned adjacent to at least said first surface of said absorbent; and
 d) deodorizing means for absorbing malodors emanating from said absorbent, said deodorizing means being an anhydrous mixture of odor absorbing particles positioned between said baffle and said absorbent, said odor absorbing particles including basic odor absorbing particles in the form of sodium bicarbonate and pH neutral odor absorbing particles in the form of a zeolite wherein a substantial amount of said sodium bicarbonate particles have a size of between about 25 and 250 micrometers and a substantial amount of said zeolite particles have a size of less than about 20 micrometers, and wherein at least 50 percent of said mixture is located in the outer 50 percent of the total surface area of said article.

12. The absorbent article of claim 11 wherein at least 75 percent of said mixture is located in the outer 50 percent of the total surface area of said article.

13. The absorbent article of claim 11 wherein at least 75 percent of said mixture is located in the outer 75 percent of the total surface area of said article.

14. The absorbent article of claim 11 wherein at least 90 percent of said mixture is located in the outer 75 percent of the total surface area of said article.

15. An absorbent article having an outer periphery, comprising:
 a) an absorbent having a first surface and a second surface aligned approximately opposite to said first surface;
 b) a liquid-impermeable baffle positioned adjacent to at least said second surface of said absorbent;
 c) a fluid-permeable cover positioned adjacent to at least said first surface of said absorbent; and
 d) deodorizing means for absorbing malodors emanating from said absorbent, said deodorizing means being an anhydrous mixture of odor absorbing particles wherein a substantial portion of sad mixture is positioned completely about said outer periphery and is located in the outer 50 percent of the total surface area of said article.

* * * * *